(12) United States Patent
Hall

(10) Patent No.: US 8,100,985 B2
(45) Date of Patent: Jan. 24, 2012

(54) METHOD FOR TREATING AN IMPLANT, AND SUCH AN IMPLANT

(75) Inventor: Jan Hall, Gothenburg (SE)

(73) Assignee: Nobel Biocare AB (publ.), Göteborg (SE)

( * ) Notice: Subject to any disclaimer, the term of this patent is extended or adjusted under 35 U.S.C. 154(b) by 1917 days.

(21) Appl. No.: 10/482,737

(22) PCT Filed: Jun. 26, 2002

(86) PCT No.: PCT/SE02/01255
§ 371 (c)(1),
(2), (4) Date: Jun. 25, 2004

(87) PCT Pub. No.: WO03/003937
PCT Pub. Date: Jan. 16, 2003

(65) Prior Publication Data
US 2005/0177248 A1    Aug. 11, 2005

(30) Foreign Application Priority Data
Jul. 4, 2001 (SE) .................................. 0102389

(51) Int. Cl.
*A61F 2/28* (2006.01)
(52) U.S. Cl. .............. 623/23.55; 623/23.53; 427/2.24
(58) Field of Classification Search .............. 623/23.55, 623/23.53, 23.57, 11.11; 427/2.24; *A61F 2/28*
See application file for complete search history.

(56) References Cited

U.S. PATENT DOCUMENTS

| | | | | |
|---|---|---|---|---|
| 5,632,779 A | * | 5/1997 | Davidson | 623/1.51 |
| 5,876,453 A | * | 3/1999 | Beaty | 433/201.1 |
| 5,947,893 A | * | 9/1999 | Agrawal et al. | 600/36 |
| 5,980,566 A | * | 11/1999 | Alt et al. | 623/23.7 |
| 6,447,550 B1 | * | 9/2002 | Hunter et al. | 623/22.15 |
| 6,461,385 B1 | * | 10/2002 | Gayer et al. | 623/23.51 |
| 6,517,888 B1 | * | 2/2003 | Weber | 427/2.24 |
| 6,689,170 B1 | * | 2/2004 | Larsson et al. | 623/23.53 |
| 6,733,503 B2 | * | 5/2004 | Layrolle et al. | 606/77 |
| 6,972,130 B1 | * | 12/2005 | Lee et al. | 424/426 |
| 2002/0198601 A1 | * | 12/2002 | Bales et al. | 623/23.55 |
| 2004/0002766 A1 | * | 1/2004 | Hunter et al. | 623/20.21 |

FOREIGN PATENT DOCUMENTS

| | | |
|---|---|---|
| WO | WO-00/72775 A1 | 12/2000 |
| WO | WO-00/72776 A1 | 12/2000 |
| WO | WO-00/72777 A1 | 12/2000 |
| WO | WO-02078759 | 10/2002 |

* cited by examiner

*Primary Examiner* — Thomas J Sweet
*Assistant Examiner* — Jason-Dennis Stewart
(74) *Attorney, Agent, or Firm* — Connolly Bove Lodge & Hutz LLP

(57) ABSTRACT

The invention relates to a method for treating an implant, and to an implant treated by said method. All or some of the outer surfaces of the implant are oxidized with a layer (1a) of substantial thickness and substantial porosity or pore volume. One or more CaP layers (12) are applied to the porous surface or surface of large pore volume. Bone-growth-stimulating agents (13), for example rh-BMP-2 or rh-BMP-7, are then applied to the CaP layer. The method and the device make it possible to support a maximum quantity of bone-growth-stimulating agent, which can be controlled in respect of its release function.

23 Claims, 2 Drawing Sheets

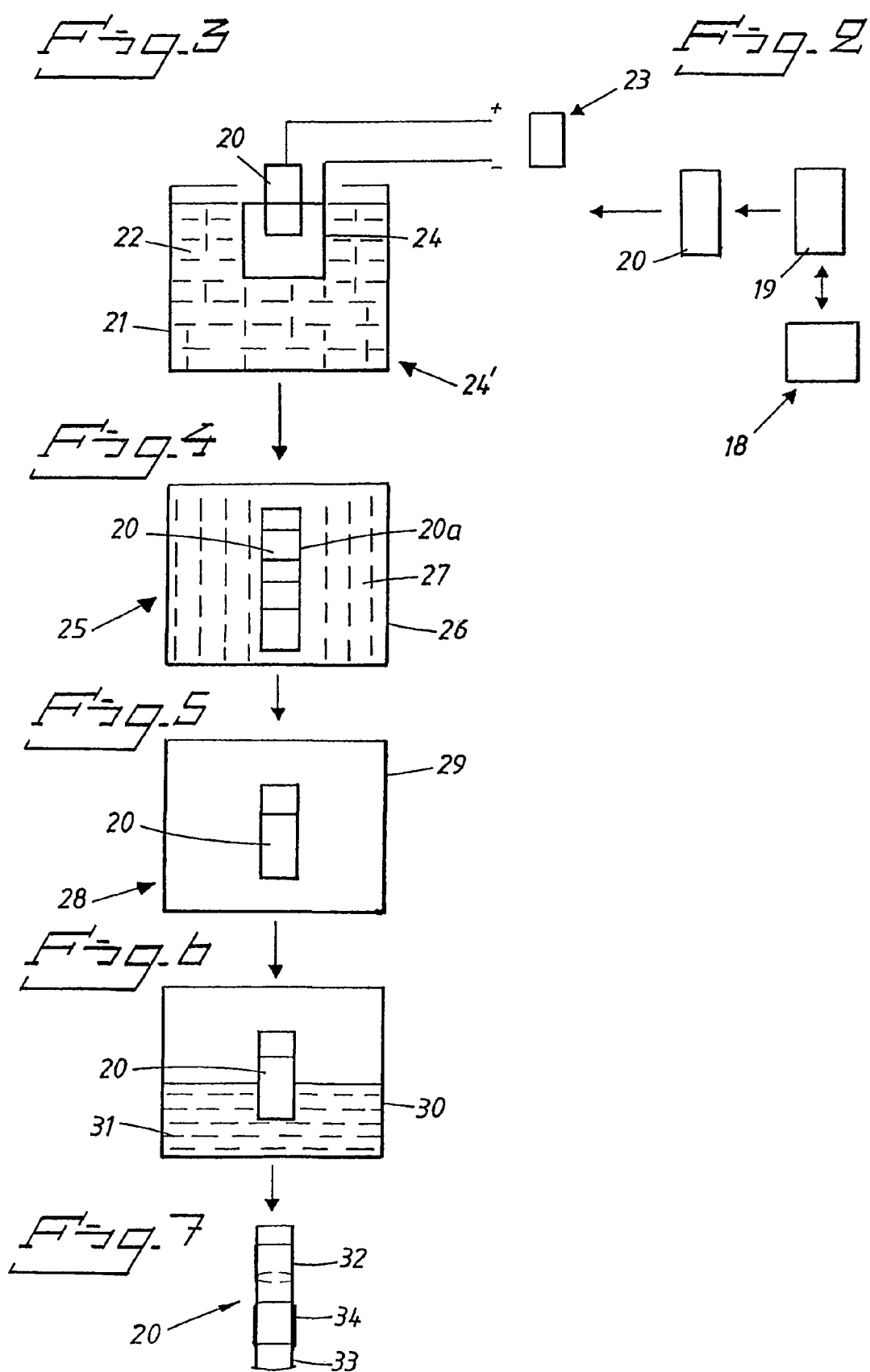

METHOD FOR TREATING AN IMPLANT, AND SUCH AN IMPLANT

Figure 1:
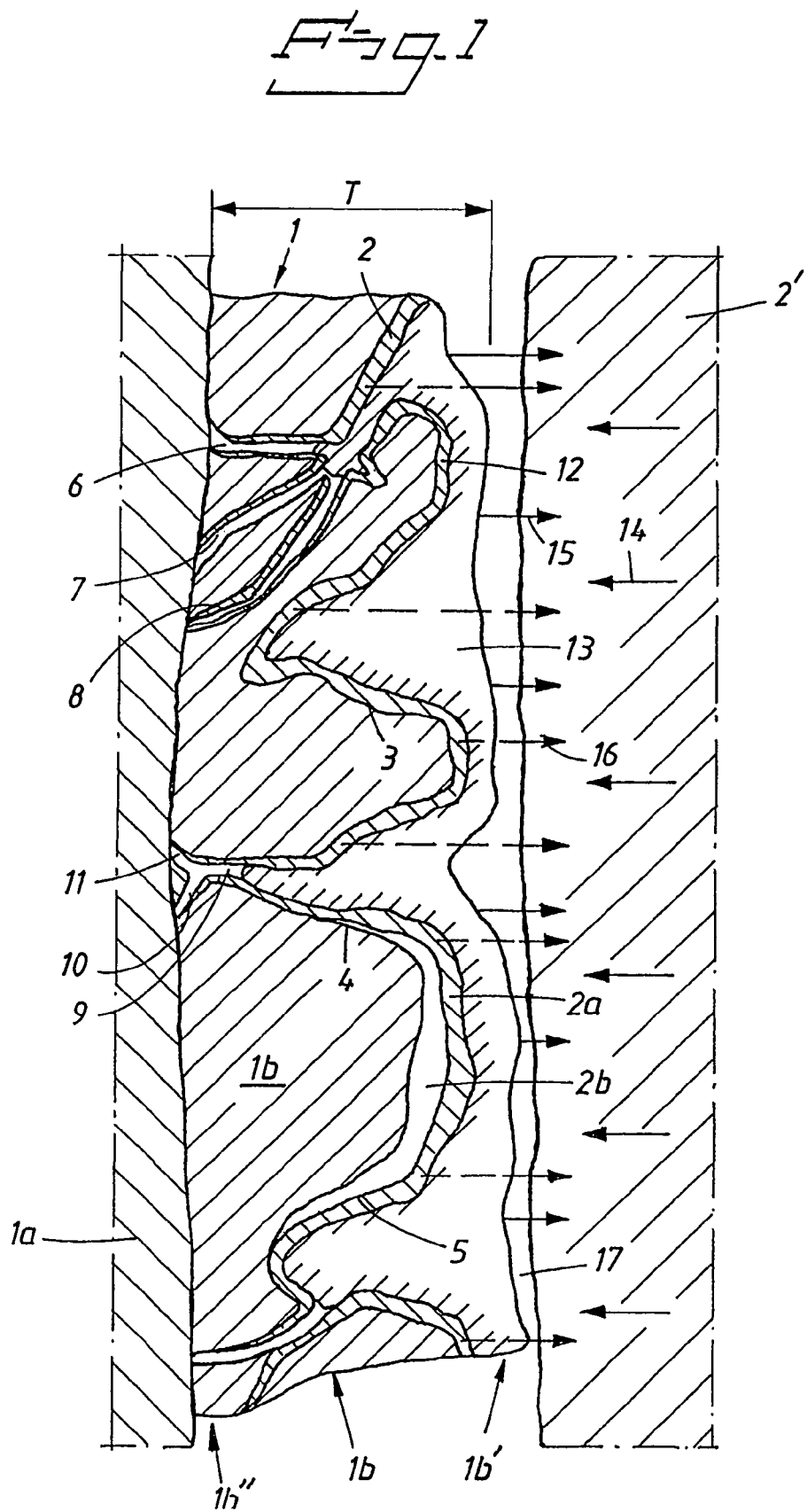

The present invention relates to a method for further treating an implant which has been made from a tissue-compatible material, preferably titanium, and is produced from a blank of said material. The invention also relates to an implant made of this tissue-compatible material.

It is also already known, in connection with implants, to use bone-growth-stimulating coatings of CaP (calcium phosphate compounds), for example in the form of HA (hydroxyapatite). These can be applied, for example, by a sputtering method in the form of so-called RF sputtering with subsequent heat treatment. In this connection, it is known to use the CaP layer as a base or depot for bone-growth-stimulating agents or substances comprising growth and differentiation factors. Such bone-growth-stimulating agents or substances comprise growth and differentiation factors and can, for example, include platelet-derived growth factor (PDGF), fibroblast growth factor (FGF), transforming growth factor (TGF) or substances belonging to the superfamily of TGF-β, such as BMP (bone morphogenetic proteins). In this connection, reference is made, inter alia, to Swedish patent application 9901973-9 filed by the same Applicant and to the relevant areas of the prior art cited therein.

In connection with implants in dental contexts, for example in the jaw bone, there is a need to achieve a high degree of individuality of treatment on account of the presence of widely varying jaw bone structures, physical responses, degrees of acidity, etc. There is therefore a need to be able to obtain the desired implant properties in different individuals who may react very differently to bone-growth-stimulating coatings or substances. By choosing the porosity and thickness of the oxide layer of the material, for example the titanium oxide layer, the implant material can itself stimulate the process of incorporation, and the use of bone-growth-stimulating coatings/agents can be combined with the choice of porosity and thickness of the oxide layer in order to afford further stimulation. The invention aims to solve this problem, inter alia, and proposes implant structures which are adapted to different treatment situations.

It is useful if coatings and agents and methods which are known per se can be used so that the desired results are unambiguous. The invention also aims to solve this problem.

In certain treatment situations, there is thus a need to be able to supply and control relatively large quantities of bone-growth-stimulating and bone-growth-maintaining agents or substances. The invention proposes, for example, principal and subsidiary depots for said coatings or substances. In this context it is a problem to combine the oxide layer structure with the layers of CaP/HA and bone-growth-stimulating agent in such a way as to obtain the most effective results in different individual cases. The invention also solves this problem.

That which can mainly be regarded as characterizing a method according to the invention is the use of three successive treatment stages. In the first treatment stage, all or some of the outer surfaces of the implant are oxidized with a layer of substantial thickness, here meaning a thickness of more than 5 μm, and with a substantial porosity or pore volume. In the second stage, calcium phosphate compound(s) (CaP), preferably in the form of hydroxyapatite (HA), are applied to the porous surface or surfaces. In the third stage, bone-growth-stimulating agent/substance is applied to the layer preferably after the application of CaP has been completed.

In further developments of the novel method, one or more first surfaces of the implant are provided with said oxide layer which is coated with either calcium phosphate compound(s) or said bone-growth-stimulating coatings or agents. One or more second surfaces on the oxide layer are coated with bone-growth-stimulating agents or said calcium phosphate compound(s), so that the first and second surfaces have oxide layers of said type, but the oxide layer is coated differently, i.e. with bone-growth-stimulating coating(s) or agents in one case and calcium phosphate compound(s) in the other.

That which can mainly be regarded as characterizing an implant according to the invention is, inter alia, that all or part of the outside of the implant is provided with an oxide layer of substantial thickness and with a pore arrangement which in one embodiment can have a substantial porosity or pore volume. The pore arrangement is in this case designed to receive one or more first layers of CaP coatings. Second layers of bone-growth-stimulating agents/substances are provided on the pore arrangement, on top of said layers of CaP/HA.

In further developments of the invention, the intermediate layer or layers of CaP/HA have a dual function, where, in a first function, the layer in question, together with the porous and thick oxide layer, forms a depot or storage base for the layer of bone-growth-stimulating agent lying on the outside. In addition, the layer of CaP/HA participates in the bone-growth-stimulating function or bone-growth-maintaining function, the CaP layer or layers preferably functioning with a longer time perspective for their release compared to the layers of bone-growth-stimulating agent.

In additional developments of the inventive concept, the implant has first and second surfaces which are provided with oxide layers but which are each provided with either CaP/HA or bone-growth-stimulating agent, so that different layer structures or coatings are present on the first and second surfaces. In a preferred embodiment, the CaP coating can have a thickness within the range of a few Angstroms and 20 μm. The bone-growth-stimulating agent layer preferably has a thickness of between a few Angstroms and 1 μm. CaP has a chosen degree of crystallization. The CaP layer can be applied by means of sputtering (e.g. magnetron sputtering) of an originally substantially amorphous CaP substance and subsequent heat treatment. When the implant material is titanium for example, the application and heat treatment of the CaP is such that depressions are obtained in the CaP layer, which can contribute to the anchoring of the bone-growth-stimulating agent layer.

Further features of the invention will become evident from the attached patent claims. By means of what has been proposed above, it is possible to satisfy treatment situations where there is a need for a maximum quantity of bone-growth-stimulating agents or substances which are intended to be supported by the implant. The structure of the oxide layer itself has properties which promote bone growth and bone incorporation and which can now be supplemented by coatings, substances and agents of said type. The time aspect of the release of the coatings, agents or substances in the implanted state can be set within wide limits. According to the invention, different parts of the implant can be provided with different combinations of oxide layers, CaP and bone-growth-stimulating agent, which can give the desired healing effects and growth effects at different levels or circumferences of the implant/jawbone. Tried and tested techniques can be used.

Presently proposed embodiments of a method and an implant according to the invention will be described below with reference to the attached drawings, in which:

FIG. 1 shows, on a very much enlarged scale, a vertical section through the implant and an oxide layer part arranged thereon and interacting with a bone, for example a jaw bone, FIG. 2 shows, in block diagram form, the production of an implant from a blank, FIGS. 3-6 show different stages of treatment of the implant produced in FIG. 2, and FIG. 7 shows, diagrammatically in a vertical view, an implant which has been treated in said stages according to FIGS. 3-6.

In FIG. 1, reference number 1 denotes an implant, or rather parts of an implant. The implant is arranged in a manner known per se in a jaw bone 2 (partially shown). The implant has a non-oxidized part 1a and an oxide layer 1b. The oxide layer has a substantial thickness T. The oxide layer is provided with a pore arrangement where, in FIG. 1, a number of pores 2, 3, 4 and 5 have been shown. The pores branch inward from the outside 1b' of the surface layer to the inside of the layer 1b" which merges into said solid part 1a. In the present case, there are pore channels which narrow inward from the outside toward the inner parts 1b" of the oxide layer. Said narrowing pore parts have been indicated by 6, 7, 8, 9, 10, 11. In accordance with the inventive concept, the appearance of the pores and channels in the layer can be varied considerably as a function of the production method and parameters of the oxide layer production. In accordance with the idea of the invention, the pore arrangement will first be provided with one or more layers of calcium phosphate compounds CaP. Said coating of CaP has been indicated by 12 in FIG. 1. Depending on the application method for the CaP layer, the layer or layers can be provided with different thicknesses, as can be seen from the figure. Thus, 2a and 2b indicate that thicker layers of CaP are present on parts of the course of the CaP layer. One or more layers of bone-growth-stimulating substance 13 have been applied on the outside of said CaP layers. Depending on the course of the oxide layer on its outside, the layer 13 can assume different thicknesses. In the present case, an example has been shown where the bone-growth-stimulating agent layer has a greater thickness than the CaP layer or layers. In other illustrative embodiments, the situation of the thicknesses can be reversed.

The bone-growth-stimulating substance 13 can be one of the bone-growth-stimulating agents or substances mentioned in the introduction, for example BMP, preferably rhBMP-2 and/or rhBMP-7.

FIG. 1 also indicates that body substances or jaw-bone substances are released after the implant has been implanted in the jaw bone for a certain time. This has been shown by arrows 14 directed toward the implant. In accordance with the invention, the substances or agents in or on the implant will be released in the opposite direction. Release of body substances and release of the implant's coatings have been indicated by arrows 15. Once a certain degree of release of the outer bone-growth-stimulating agent layer has occurred, release of the CaP layer or layers starts, which has been indicated by broken arrows 16. The substances pass into the space or gap between the jaw bone and the implant, which gap will be filled by bone growth in the jaw bone 2. Said bone growth also causes the jaw bone to grow into the pore system and, on release of both the bone-growth-stimulating agent layer and the CaP layer, the bone growth cooperates with the pore system and the titanium oxide in the latter, which, in accordance with the above, itself also stimulates the bone growth.

In the block diagram in FIG. 2, reference number 18 denotes a production apparatus or production station for implants. The production involves the working of blanks of tissue-compatible material, preferably in the form of titanium 19. One such blank has been indicated by 19. An implant 20 is collected from the station 18 and will be treated further in the functional stages according to FIGS. 3, 4, 5 and 6.

In FIG. 3, the oxide layer is produced on all or part of the implant 20 by means of anodic oxidation, which is an electrochemical method. The relevant surfaces of the implant are exposed so that, upon immersion into a vessel 21 containing electrolyte 22, oxidation of the surfaces in question takes place. The method is known per se and will therefore not be described here. It will however be noted that the method uses a voltage source 23 and a cathode 24. Before the treatment in the station according to FIG. 3, the implant has been mechanically worked by turning, milling, polishing, etching, etc. Those parts of the implant which are not to be provided with oxide layers are masked in a manner known per se. The structure of the oxide layer can be affected by a number of parameters in the process, for example the electrolyte's composition and temperature, the voltage applied and current, the electrode geometry, treatment time, etc. The station as such is indicated by 24 in FIG. 3. After preparation in the station 24, the implant 20 is transferred to the station 25 according to FIG. 4. The outer parts 20a or relevant surface parts of the implant will be provided in whole or in part with a film-like or layer-like coating or coatings. This can be done in a manner known per se in a chamber 26, and the coating can be applied by means of so-called "RF sputtering" or "magnetron sputtering". In this connection, reference may be made, inter alia, to the PCT application WO 98/48862. In the chamber, one or more calcium phosphate compounds 27 are applied or sputtered onto the surface or surface parts of the implant. The implant 20 is then transferred to an oven 28 in which the implant undergoes heat treatment. Temperatures, for example of 600° C., and times for treatment in saturated water vapour can be chosen. The heat treatment gives partial crystallization of the coating applied in the chamber 26. In the present case, a suitable degree of crystallization is between 25-75%, which will be set in relation to the degree of crystallization 0% applicable to the radiologically amorphous surface where the particle size is ca. 50 nm. The degree of crystallization can be 25-75% or 75-100%, for example. In the case of three layers or coatings, for example, the degree of crystallization in layer 1 can be 75-100%, and in layer 2 it can be 25-100%, while layer 3 is amorphous.

After treatment in the oven 29, the implant 20 is transferred to the station according to FIG. 6 for application of bone-growth-stimulating agent in accordance with the above. According to FIG. 6, a vessel 30 is used in which a solution of bone-growth-stimulating agent is indicated by 31. The immersion takes place for a chosen time which is set in relation to the release function of the bone-growth-stimulating agent layer (wet chemical deposition) on the implant, the drying time and/or another parameter.

FIG. 7 shows the fully treated implant. The implant can, for example, comprise three different surfaces 32, 33, 34, all of the surfaces being provided with the described oxide layer, a first surface 32 being provided with only CaP, a second surface 33 being provided with only bone-growth-stimulating agent, and the surface 34 being provided with both CaP and bone-growth-stimulating agent according to FIG. 1.

The CaP coating can have a thickness within the range of a few Angstroms and 20 μm, while the bone-growth-stimulating agent layer can have a thickness of between a few Angstroms and 1 μm. Said values are to be regarded as average values (cf. the layer 13 in FIG. 1). The oxide layer can have a surface roughness within the range of 0.4-5 μm. The oxide layer is highly porous with a pore number of $1 \times 10^7$-$1 \times 10^{10}$ pores/cm$^2$. Each oxide layer surface has mainly pores with diameter sizes within the range of 0.1-10 μm and/or a total pore volume which lies within a range of $5 \times 10^{-2}$ and $10^{-5}$ cm$^3$. The inner layers can have a higher degree of crystallization than the outside layers, and the innermost CaP layer can thus have a degree of crystallization of 75-100%.

The invention is not limited to the embodiment shown above by way of example, and instead it can be modified within the scope of the attached patent claims and the inventive concept.

The invention claimed is:

1. A method for further treating an implant of tissue-compatible material and produced from a blank of said material characterized in that:
   a) all or some of the outer surfaces of the implant are oxidized with a layer of substantial thickness and with a substantial porosity of pore volume, wherein the thickness of the layer is more than 5 µm,
   b) calcium phosphate compound(s) (CaP) are applied to the porous surface, and
   c) bone-growth-stimulating agent/substance is then applied on the outside or on top of the calcium phosphate compound(s).

2. The method as claimed in claim 1, characterized in that one or more surfaces are provided with said oxide layers which are coated with either calcium phosphate compound(s) or said bone-growth-stimulating agents.

3. The method as claimed in claim 1 wherein said tissue-compatible material comprises titanium.

4. The method as claimed in claim 1 wherein all or some of the outer surface of the implant are oxidized by anodization.

5. The method as claimed in claim 1 wherein the bone-growth-stimulating agent/substance is applied on the outside or on top of the calcium phosphate compound(s) after the latter has or have been applied completely or dried completely.

6. The implant as claimed in claim 1 wherein said tissue-compatible material comprises titanium.

7. The implant as claimed in claim 1 wherein said CaP comprises HA.

8. The implant as claimed in claim 1 wherein said oxide layer has a pore number of $1 \times 10^7$ to $1 \times 10^{10}$ pores/$cm^2$.

9. The implant as claimed in claim 1 wherein said oxide layer has mainly pores with diameters of 0.1 to 10 µm or a total pore volume of $5 \times 10^{-2}$ to $10^{-5}$ $cm^3$ or both.

10. The implant as claimed in claim 1 wherein said oxide layer has a surface roughness of 0.4-5 µm.

11. An implant made of tissue-compatible material, characterized by the following combination of elements:
    a) all or part of the outside of the implant is provided with an oxide layer of substantial thickness and with a pore arrangement which has a substantial porosity or pore volume, wherein the thickness of the layer is more than 5 µm,
    b) one or more first layers or coatings of calcium phosphate compound or calcium phosphate compounds are provided on the pore arrangement, and
    c) a second layer of bone-growth-stimulating agent/substance is provided on the pore arrangement, on top of said first layers.

12. The implant as claimed in claim 11, characterized in that the layer (2) of CaP has dual functions, namely, on the one hand, together with the porous and thick oxide layer, to form a depot for the layer of bone-growth-stimulating agent or substance lying on the outside, and, on the other hand, to participate in the bone-growth-stimulating function.

13. The implant as claimed in patent claim 12, characterized in that surfaces which have said oxide layers are coated with either CaP or with bone-growth-stimulating agent.

14. The implant as claimed in patent claim 12, characterized in that surface that do not have a porous oxidation layer are coated with CaP and bone-growth-stimulating agent or with CaP or bone-growth-stimulating agent alone.

15. The implant as claimed claim 11, characterized in that first surfaces which have said oxide layers are coated with either CaP or with bone-growth-stimulating agent.

16. The implant as claimed in claim 11, characterized in that surface that do not have a porous oxidation layer are coated with CaP and bone-growth-stimulating agent or with CaP or bone- growth-stimulating agent alone.

17. The implant as claimed in claim 11, characterized in that the oxide layer forms a main depot for CaP/HA and bone-growth-stimulating agent and the CaP/HA layer forms a subordinate anchoring depot for bone-growth-stimulating agent.

18. The implant as claimed in claim 11, characterized in that the CaP coating has a thickness within the range of a few Angstroms and 20 pm, and in that each bone-growth-stimulating agent layer has a thickness of between a few Angstroms and 1 µm.

19. The implant as claimed in claim 11, characterized in the that the respective Cap layer constitutes a substantially amorphous CaP substance sputtered into a CaP surface or implant surface which has a different degree of crystallinity by means of a subsequent heat treatment.

20. The implant as claimed in claim 11, characterizedin that the CaP layer is formed with depressions which contribute to increasing the stability of bone-growth-stimulating agent in the CaP layer.

21. The implant as claimed in claim 11, characterized in that the CaP layer has a degree of crystallization of 25-75 %.

22. The implant as claimed in claim 11, characterized in that the CaP layer or coating has a degree of crystallization of 75-100 %.

23. The implant as claimed in claim 11, characterized in that layer with different degrees of crystallization are provided, and in that, in the case of three layers for example, the first layer has a degree of crystallization of 75-100 %, the second layer has a degree of crystallization of 25-75 %, and the third layer is amorphous.

* * * * *